United States Patent
Coronado et al.

(10) Patent No.: US 7,378,130 B2
(45) Date of Patent: May 27, 2008

(54) METHOD OF MAKING A GRAPHICALLY-PRINTED COMPONENT FOR AN ABSORBENT DISPOSABLE ARTICLE

(75) Inventors: Nicte Coronado, San Luis Potosi (MX); Fermin Ruiz, Veracruz (MX); Jorge Santisteban, San Luis Potosi (MX)

(73) Assignee: Polymer Group, Inc., Charlotte, NC (US)

( * ) Notice: Subject to any disclaimer, the term of this patent is extended or adjusted under 35 U.S.C. 154(b) by 0 days.

(21) Appl. No.: 10/818,793

(22) Filed: Apr. 6, 2004

(65) Prior Publication Data

US 2005/0095941 A1    May 5, 2005

Related U.S. Application Data

(60) Provisional application No. 60/462,056, filed on Apr. 11, 2003.

(51) Int. Cl.
*B05D 1/36* (2006.01)
*B05D 3/12* (2006.01)

(52) U.S. Cl. .................. 427/261; 427/177; 427/179; 427/359; 427/362; 427/365; 427/366

(58) Field of Classification Search ............... 442/401
See application file for complete search history.

(56) References Cited

U.S. PATENT DOCUMENTS

| | | | | |
|---|---|---|---|---|
| 5,256,717 A | * | 10/1993 | Stauffer et al. | 524/293 |
| 5,458,590 A | * | 10/1995 | Schleinz et al. | 604/361 |
| 6,231,557 B1 | * | 5/2001 | Krautkramer et al. | 604/385.16 |
| 6,949,689 B2 | * | 9/2005 | Noda et al. | 604/361 |
| 2004/0038607 A1 | * | 2/2004 | Williamson et al. | 442/101 |

FOREIGN PATENT DOCUMENTS

| | | | |
|---|---|---|---|
| JP | 11-151785 | * | 6/1999 |
| WO | WO 00/07533 | * | 2/2000 |

* cited by examiner

*Primary Examiner*—William Phillip Fletcher, III
(74) *Attorney, Agent, or Firm*—Kilyk & Bowersox, PLLC; Valerie Calloway

(57) ABSTRACT

The present invention is directed to a method for making a graphically-printed component for an absorbent disposable article. The method comprises providing a molten polymer by feeding polymer chips into an extruder and melting the polymer chips. The molten polymer is extruded in the form of a thermoplastic polymer film onto a provided nonwoven fabric in an in-line process, in which the film has a basis weight of about 10 gsm, to provide a backsheet comprising the film and the nonwoven fabric. The backsheet on the film is graphically printed with printing means to provide a graphically printed backsheet. The graphically printed back sheet is wound into a roll good, or an absorbent core is positioned between it and a liquid permeable topsheet to provide an absorbent disposable article.

18 Claims, 1 Drawing Sheet

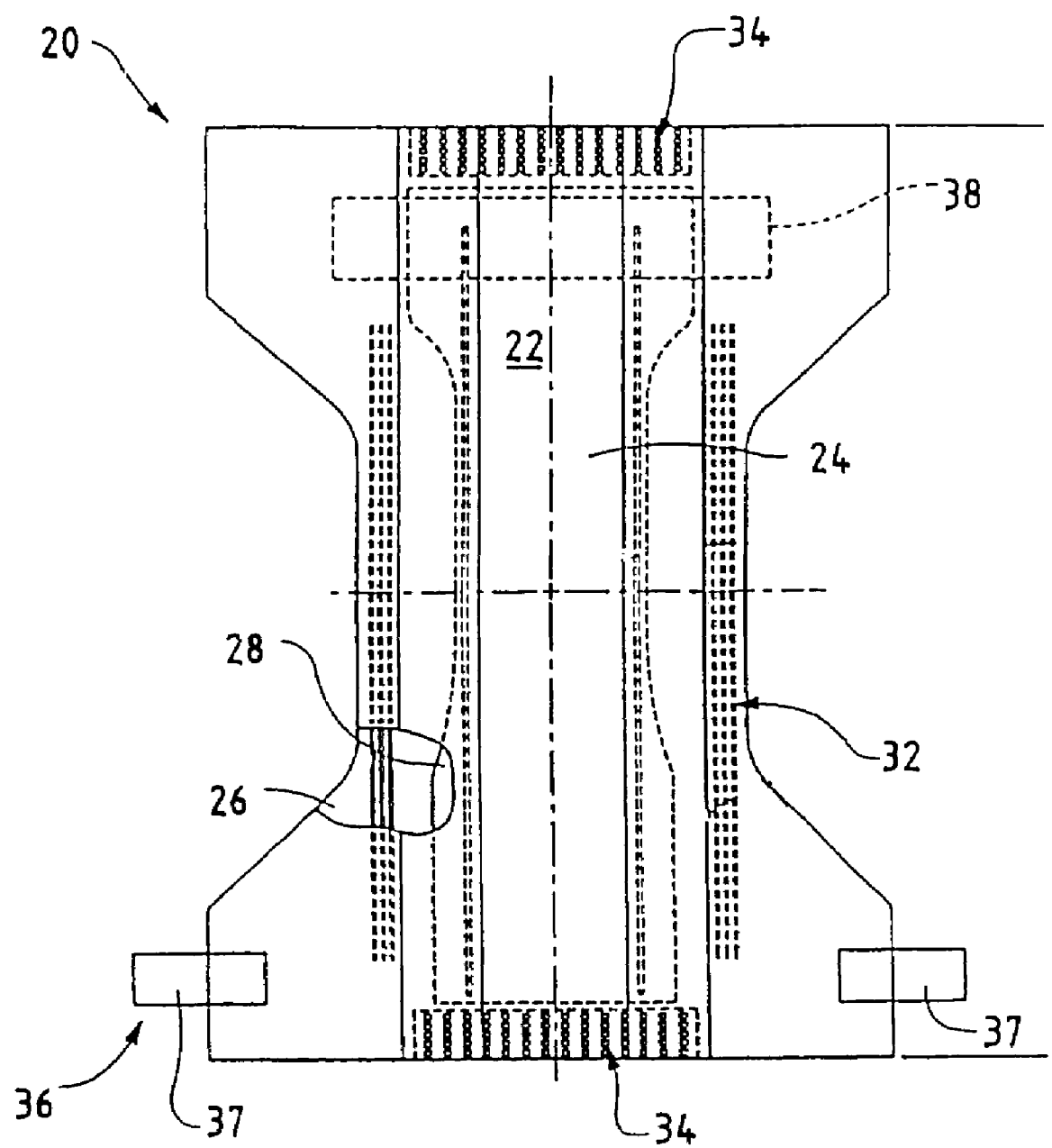

METHOD OF MAKING A GRAPHICALLY-PRINTED COMPONENT FOR AN ABSORBENT DISPOSABLE ARTICLE

TECHNICAL FIELD

The present invention is directed to a nonwoven laminate, and more particularly, to a nonwoven laminate printed with graphics, which exhibits a soft cloth-like feel and is lightweight, suitable for application as a backsheet in disposable absorbent hygiene articles and medical/industrial protective end-use articles.

BACKGROUND OF THE INVENTION

Films are used in a wide variety of applications where the engineered qualities of the apertured and/or unapertured film can be advantageously employed as a component substrate. The use of selected thermoplastic polymers in the construction of film products, selected treatment of the polymeric films (either while in melt form or in an integrated structure), and selected use of various mechanisms by which the film is integrated into a useful construct, are typical variables by which to adjust and alter the performance of the resultant polymeric film product.

The formation of finite thickness films from thermoplastic polymers is a well known practice. Thermoplastic polymer films can be formed by either dispersion of a quantity of molten polymer into a mold having the dimensions of the desired end product, known as a thermo-formed or injection-molded film, or by continuously forcing the molten polymer through a die, known as an extruded film. Extruded thermoplastic polymer films can either be formed such that the film is cooled then wound as a completed product, or dispensed directly onto a substrate material to form a composite material having performance of both the substrate and the film layers.

The application of the extruded film directly onto a substrate material imparts the substrate material with enhanced physical properties. It is known in the art that the application of a thermoplastic polymer film having suitable flexibility and porosity onto a nonwoven fabric results in a composite material having significant barrier properties and is suitable for disposable protective garment manufacture.

Film substrates are desirable for a variety of end-use applications due to the barrier performance such substrates can provide. Films have proven to be particularly suitable for a variety of medical, hygiene, and industrial applications and when utilized in a laminate construct, permits cost-effective, disposable use. Use of such materials for diapers, sanitary napkins, medical wipes, and the like has become increasingly widespread, since the use of a nonwoven fabric constructs can provide a desired softness that may be required for specific hygiene applications, such as a backsheet for a disposable absorbent garment.

The use of disposable sanitary articles, and in particular disposable diapers, has come into public favor over the past twenty years due to the convenience of use. There is an ever-present demand to improve the comfort and aesthetics of the article. Recently, a soft, cloth-like backsheet has become desirable so as to reduce the amount of noise made by the diaper during an infant's activities, as well as during donning and doffing the disposable diaper. Further, it has become desirable to impart a graphical image onto the backsheet of the diaper, such as figures, animals or characters, in order to impart aesthetic appeal to the disposable article.

Traditionally, the method of making a printed backsheet for an absorbent article consists of bonding a roll of previously printed thermoplastic film to a pre-formed roll of nonwoven fabric. The film tends to have a heavier basis weight due to the problems associated with unwind tension and breakage with lighter weight films, which slows the printing and bonding processes. A need exists for an in-line process that is more efficient and allows for a lighter basis weight film to be utilized with a nonwoven that exhibits a cloth-like feel, wherein the resultant laminate exhibits the necessary barrier performance, as well as conformability for comfort when used as a backsheet for an absorbent article.

SUMMARY OF THE INVENTION

The present invention is directed to a nonwoven laminate printed with graphics, which exhibits a soft cloth-like feel, is lightweight, and impermeable, and suitable for application as a backsheet in disposable absorbent hygiene articles, in addition to medical/industrial protective end-use articles.

In accordance with the present invention, the graphically printed nonwoven laminate is produced in-line, wherein the weight of the construct can be considerably reduced due to direct extrusion of the film onto the nonwoven. Subsequent to the laminating process, the laminate is immediately printed with the desired graphical designs and wound as a rolled good. The resultant laminate is lightweight, as well as impermeable, making it especially suitable for a backsheet.

The film composition may include the following olefin polymers, but not limited to, isotactic polypropylene, linear low-density polyethylene, low-density polyethylene, high-density polyethylene, amorphous polypropylene, polybutylene, ethylene/vinyl acetate copolymer, ethylene/ethyl acrylate copolymer, ethylene/methyl acrylate copolymer, polystyrene, polyurethane and the combination thereof.

The nonwoven substrate to receive the extruded film is comprised of one or more layers. Nonwoven layers may include carded, spunmelt, spunlace and combination thereof, for example, spunbond, meltblown, thermalbond, spunlace, and airlaid. Further, such continuous and discontinuous extruded filaments, may optionally be comprised of fine denier or nano-denier filaments. Formation of fabrics from nano-denier barrier materials, particularly when a light basis weight nano-denier barrier layer is either coated or "dusted" onto a substrate layer or is combined with one or more conventional barrier layers, can provide enhanced barrier and aesthetic properties. The present invention allows for the in-line production of a graphically printed nonwoven laminate that is light weight and suitable for use as a barrier fabric, particularly for disposable absorbent article applications, such as diapers and incontinence devices.

BRIEF DESCRIPTION OF THE DRAWINGS

FIG. 1 is a diagrammatic view of a disposable diaper.

DETAILED DESCRIPTION

While the present invention is susceptible of embodiment in various forms, hereinafter is described a presently preferred embodiment of the invention, with the understanding that the present disclosure is to be considered as an exemplification of the invention, and is not intended to limit the invention to the specific embodiment illustrated.

The formation of finite thickness films from thermoplastic polymers is a well-known practice. Thermoplastic polymer films can be formed by either dispersion of a quantity of molten polymer into a mold having the dimensions of the desired end product, known as a cast film, or by continuously forcing the molten polymer through a die, known as an extruded film. Extruded thermoplastic polymer films can either be formed such that the film is cooled then wound as a completed product, or dispensed directly onto a substrate material to form a composite material having performance of both the substrate and the film layers.

Extruded films can be formed in accordance with the following representative direct extrusion film process. Blending and dosing storage comprising at least two hopper loaders, feed into two variable speed augers. The variable speed augers transfer predetermined amounts of polymer chip into a mixing hopper. The mixing hopper contains a mixing propeller to further the homogeneity of the polymer or a polymer mixture. The polymer chip feeds into a multi-zone extruder. Upon mixing and extrusion from multi-zone extruder, the polymer compound is conveyed via heated polymer piping through screen changer, wherein breaker plates having different screen meshes are employed to retain solid or semi-molten polymer chips and other macroscopic debris. The polymer is then fed into a melt pump, and then to a combining block. The combining block allows for multiple film layers to be extruded, the film layers being of either the same composition or fed from different systems as described above. The combining block is connected to an extrusion die, which is positioned in an overhead orientation such that molten film extrusion is deposited at a nip between a nip roll and a cast roll.

The molten polymer from the extrusion die is deposited directly onto the substrate material at the nip point between the nip roll and the cast roll. The newly formed nonwoven laminate is then immediately printed with the desired graphics and wound as a roll good.

A nonwoven layer, which may also include fine denier and nano-denier fabrics, is to receive the extruded molten polymer. In general, continuous filament nonwoven fabric formation involves the practice of the spunbond process. A spunbond process involves supplying a molten polymer, which is then extruded under pressure through a large number of orifices in a plate known as a spinneret or die. The resulting continuous filaments are quenched and drawn by any of a number of methods, such as slot draw systems, attenuator guns, or Godet rolls. The continuous filaments are collected as a loose web upon a moving foraminous surface, such as a wire mesh conveyor belt. When more than one spinneret is used in line for the purpose of forming a multi-layered fabric, the subsequent webs is collected upon the uppermost surface of the previously formed web. The web is then at least temporarily consolidated, usually by means involving heat and pressure, such as by thermal point bonding. Using this means, the web or layers of webs are passed between two hot metal rolls, one of which has an embossed pattern to impart and achieve the desired degree of point bonding, usually on the order of 10 to 40 percent of the overall surface area being so bonded.

A related means to the spunbond process for forming a layer of a nonwoven fabric is the melt blown process. Again, a molten polymer is extruded under pressure through orifices in a spinneret or die. High velocity air impinges upon and entrains the filaments as they exit the die. The energy of this step is such that the formed filaments are greatly reduced in diameter and are fractured so that microfibers of finite length are produced. This differs from the spunbond process whereby the continuity of the filaments is preserved. The process to form either a single layer or a multiple-layer fabric is continuous, that is, the process steps are uninterrupted from extrusion of the filaments to form the first layer until the bonded web is wound into a roll. Methods for producing these types of fabrics are described in U.S. Pat. No. 4,043,203, incorporated herein by reference Additionally, suitable nano-denier continuous filament layers can be formed by either direct spinning of nano-denier filaments or by formation of a multi-component filament that is divided into nano-denier filaments prior to deposition on a substrate layer. U.S. Pat. No. 5,678,379 and No. 6,114,017, both incorporated herein by reference, exemplify direct spinning processes practicable in support of the present invention. U.S. Pat. No. 5,678,379 and No. 6,114,017, both incorporated herein by reference, exemplify direct spinning processes practicable in support of the present invention.

It is also within the purview of the present invention that the nonwoven layer of the film/nonwoven laminate be comprised of one or more layers, wherein the layers may be of similar or dissimilar compositions and manufacturing process. For example, the layers may be comprised of a SMS (spunbond-meltblown-spunbond), SMMS, SS, SSS, or a combination thereof. Further, the layers may optionally incorporate a thermalbond, spunlace, airlaid fabric, or combination thereof. Further still, one or more of the layers may comprise a three-dimensional image or pattern imparted by a three-dimensional image transfer device. Such three-dimensional image transfer devices are disclosed in U.S. Pat. No. 5,098,764, which is hereby incorporated by reference; with the use of such image transfer devices being desirable for providing a fabric with enhanced physical properties as well as an aesthetically pleasing appearance.

The newly formed nonwoven laminate is immediately printed with the desired graphics by way of flexographic printing or rotogravure printing. The flexographic printing process is known to produce precise graphical reproductions of a variety of subject matter, such as figures, animals, characters, etc., imparting aesthetic appeal to the garment. Representative flexographic printing processes are reported in U.S. Pat. No. 4,186,661, No. 5,015,556, and No. 5,322,761, and are hereby incorporated by reference. A rotogravure printing process may be used as well. Suitable rotogravure printing methods are exemplified in U.S. Pat. No. 4,239,001 and No. 5,497,700, both hereby included by reference. In addition to the aforementioned printing processes, it is also possible to use alternate printing techniques, including, but not limited to screen printing, thermal transfer, electrostatic image transfer, and inkjet printing. Further, the printing inks of the present invention may be either solvent base, water base inks or UV inks. In addition to the immediate application of printed graphics to the film side of laminate, it is also within the purview of the invention to include the printed graphics on the nonwoven side of the laminate.

In one embodiment, a diaper backsheet was constructed from a 9 gsm low density polyethylene, which was extruded onto a 13 gsm spunbond-spunbond construct. The laminate was then printed with the desired graphics on the film side by a flexographic process.

The fabric of the present invention may be utilized in a variety of hygienic, medical, and industrial applications. Suitable hygiene applications include, but are not limited to disposable baby changing pads, wherein the foreground of the fabric can be treated with various different surfactants so as to control the absorption of liquid insults. Further, the fabric is suitable for use as a hygienic wipe, such as a facial or other cleansing wipe.

Disposable waste-containment garments, are generally described in U.S. Patents No. 4,573,986, No. 5,843,056, and No. 6,198,018, which are incorporated herein by reference.

An absorbent article incorporating the lightweight, cloth-like, impermeable backsheet of the present invention is represented by the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments, training pants, pull-on garments, and the like, as well as other articles such as feminine hygiene wrappers.

FIG. 1 is a plan view of a diaper 20 in an uncontracted state (i.e., with elastic induced contraction pulled out) with portions of the structure being cut-away to more clearly show the construction of the diaper 20. As shown in FIG. 1, the diaper 20 preferably comprises a containment assembly 22 comprising a liquid pervious topsheet 24; a liquid impervious backsheet 26 joined to the topsheet; and an absorbent core 28 positioned between the topsheet 24 and the backsheet 26. The absorbent core 28 has a pair of opposing longitudinal edges, an inner surface and an outer surface. The diaper can further comprise elastic leg features 32; elastic waist features 34; and a fastening system 36 which preferably comprises a pair of securement members 37 and a landing member 38.

Catamenial products, such as feminine hygiene pads, are of the same general construction as the aforementioned diaper structure. Again, a topsheet and a backsheet are affixed about a central absorbent core. The overall design of the catamenial product is altered to best conform to the human shape and for absorbing human exudates. Representative prior art to such article fabrication include U.S. Pat. No. 4,029,101, No. 4,184,498, No. 4,195,634, and No. 4,886,513, which are incorporated herein by reference.

From the foregoing, numerous modifications and variations can be effected without departing from the true spirit and scope of the novel concept of the present invention. It is to be understood that no limitation with respect to the specific embodiments disclosed herein is intended or should be inferred. The disclosure is intended to cover, by the appended claims, all such modifications as fall within the scope of the claims.

What is claimed is:

1. A method for making a graphically-printed backsheet for an absorbent disposable article, comprising the steps of:
    a. providing a molten polymer comprising feeding polymer chips into an extruder and melting said polymer chips with heating thereof to provide said molten polymer;
    b. providing a nonwoven fabric;
    c. providing a printing means;
    d. extruding said molten polymer in the form of a thermoplastic polymer film onto said nonwoven fabric in an in-line process, wherein said thermoplastic polymer film has a basis weight of about 10 gsm, to provide a backsheet comprising the thermoplastic polymer film and the nonwoven fabric;
    e. graphically printing said backsheet on the thermoplastic polymer film thereof with said printing means, to provide a graphically printed backsheet; and
    f. winding said graphically printed backsheet into a roll good.

2. A method for making a graphically-printed backsheet as in claim 1, wherein the thermoplastic polymer film is a low density polyethylene.

3. A method for making a graphically-printed backsheet as in claim 1, wherein said nonwoven fabric is selected from the group consisting of spunbond, meltblown, thermalbond, spunlace, airlaid, and the combinations thereof.

4. A method for making a graphically-printed backsheet as in claim 1, wherein said nonwoven fabric comprises two adjacent layers of spunbond material.

5. A method for making a graphically-printed backsheet as in claim 1, wherein said printing means is a flexographic printing process.

6. A method for making a graphically-printed back sheet as in claim 1, wherein said extruding of said molten polymer comprises directly dispensing said thermoplastic polymer film onto said nonwoven fabric wherein said film comprises low density polyethylene.

7. A method for making a graphically printed nonwoven laminate for an absorbent disposable article, comprising the steps of:
    a. providing a molten polymer comprising feeding polymer chips into an extruder and melting said polymer chips with heating thereof to provide said molten polymer;
    b. providing a nonwoven fabric;
    c. providing a printing means;
    d. extruding said molten polymer in the form of a thermoplastic polymer film directly onto said nonwoven fabric in an in-line process, wherein said film has a basis weight of about 10 gsm, to provide a backsheet comprising the thermoplastic polymer film and the nonwoven fabric;
    e. graphically printing said backsheet on the thermoplastic polymer film thereof with said printing means, to provide a liquid-impermeable graphically printed backsheet; and
    f. positioning an absorbent core between said printed backsheet and a liquid-permeable top sheet.

8. A method for making a graphically-printed backsheet as in claim 1, wherein said graphically printing comprises directly applying printing inks to the thermoplastic polymer film.

9. A method for making a graphically-printed backsheet as in claim 1, wherein said providing of said molten polymer comprises feeding solid polymer chips into said extruder and feeding the molten polymer formed from melting the polymer chips to an extrusion die, and wherein said extruding of said molten polymer comprises directly extruding said molten polymer as a molten film from the extrusion die onto said nonwoven fabric.

10. A method for making a graphically-printed backsheet as in claim 9, wherein said feeding of said molten polymer formed from melting the polymer chips to said extrusion die comprises conveying said molten polymer from said extruder via heated piping through a screen retaining solid or semi-molten polymer chips to provide a screen molten polymer, and then feeding said screened molten polymer into a melt pump and from the melt pump to a combining block connected to said extrusion die for depositing said extruded thermoplastic polymer film formed from the molten polymer directly onto the nonwoven fabric.

11. A method for making a graphically-printed backsheet as in claim 9, wherein the molten film is deposited on the nonwoven fabric at a nip between a nip roll and a cast roll.

12. A method for making a graphically-printed backsheet as in claim 9, wherein the molten film consists of olefin thermoplastic polymer.

13. A method for making a graphically printed nonwoven laminate for an absorbent disposable article as in claim 7, wherein said graphically printing comprises directly applying printing inks to the thermoplastic polymer film.

14. A method for making a graphically printed nonwoven laminate for an absorbent disposable article as in claim 7, wherein said providing of said molten polymer comprises feeding solid polymer chips into said extruder and feeding the molten polymer formed from melting the polymer chips to an extrusion die, and wherein said extruding of said molten polymer comprises directly extruding said molten polymer as a molten film from the extrusion die onto said nonwoven fabric.

15. A method for making a graphically printed nonwoven laminate for an absorbent disposable article as in claim 14, wherein said feeding of said molten polymer formed from melting the polymer chips to said extrusion die comprises conveying said molten polymer from said extruder via heated piping through a screen retaining solid or semi-molten polymer chips to provide a screen molten polymer, and then feeding said screened molten polymer into a melt pump and from the melt pump to a combining block connected to said extrusion die for depositing said extruded thermoplastic polymer film formed from the molten polymer directly onto the nonwoven fabric.

16. A method for making a graphically printed nonwoven laminate for an absorbent disposable article as in claim 14, wherein the molten film is deposited on the nonwoven fabric at a nip between a nip roll and a cast roll.

17. A method for making a graphically printed nonwoven laminate for an absorbent disposable article as in claim 14, wherein the molten film consists of olefin thermoplastic polymer.

18. A method for making a graphically printed nonwoven laminate for an absorbent disposable article as in claim 14, wherein said graphically printing comprises directly applying printing inks to the thermoplastic polymer film.

* * * * *